United States Patent
Vu et al.

(10) Patent No.: US 11,441,838 B2
(45) Date of Patent: Sep. 13, 2022

(54) PROCESSES FOR RECOVERING LPG FROM A REFORMING-ZONE EFFLUENT

(71) Applicant: UOP LLC, Des Plaines, IL (US)

(72) Inventors: Thuy T. Vu, Buffalo Grove, IL (US); Robert E. Tsai, Arlington Heights, IL (US); Xin X. Zhu, Long Grove, IL (US); Amit Goyal, Haryana (IN); William Yanez, Crystal Lake, IL (US); Sudipta K. Ghosh, Haryana (IN)

(73) Assignee: UOP LLC, Des Plaines, IL (US)

( * ) Notice: Subject to any disclaimer, the term of this patent is extended or adjusted under 35 U.S.C. 154(b) by 877 days.

(21) Appl. No.: 16/278,017

(22) Filed: Feb. 15, 2019

(65) Prior Publication Data

US 2020/0263922 A1    Aug. 20, 2020

(51) Int. Cl.
| | | |
|---|---|---|
| *F25J 3/02* | (2006.01) | |
| *C01B 3/34* | (2006.01) | |
| *C01B 3/52* | (2006.01) | |
| *C07C 7/00* | (2006.01) | |

(52) U.S. Cl.
CPC .............. *F25J 3/0242* (2013.01); *C01B 3/34* (2013.01); *C01B 3/52* (2013.01); *C07C 7/005* (2013.01); *F25J 3/0247* (2013.01); *F25J 3/0252* (2013.01); *C01B 2203/0227* (2013.01);
(Continued)

(58) Field of Classification Search
CPC .. F25J 3/02; F25J 3/0242; F25J 3/0252; F25J 2230/08; C01B 3/34; C01B 3/52; C01B 2203/0227; C01B 2203/0415; C01B 2203/048; C01B 2203/124
See application file for complete search history.

(56) References Cited

U.S. PATENT DOCUMENTS

| | | |
|---|---|---|
| 3,470,084 A | 9/1969 | Scott |
| 4,129,496 A | 12/1978 | Loboda |
| 4,212,726 A | 7/1980 | Mayes |

(Continued)

FOREIGN PATENT DOCUMENTS

| | | | |
|---|---|---|---|
| WO | 2016069404 A1 | 5/2016 | |
| WO | WO-2016069404 A1 * | 5/2016 | ............. B01D 53/04 |

OTHER PUBLICATIONS

International search report from corresponding PCT application No. PCT/US2020/017880, dated May 28, 2020.
(Continued)

*Primary Examiner* — Youngsul Jeong (57) ABSTRACT

Embodiments of apparatuses and methods for reforming of hydrocarbons including recovery of products are provided. In one example, a method comprises separating a reforming-zone effluent into a net gas phase stream and a liquid phase hydrocarbon stream. The net gas phase stream is separated for forming an $H_2$-rich stream and a first liquid phase hydrocarbon stream. The $H_2$-rich stream may be contacted with an adsorbent to form an $H_2$-ultra rich stream and a gas stream. $C_3/C_4$ hydrocarbons are absorbed from the gas stream with the liquid phase hydrocarbon stream. The gas stream may be contacted with an $H_2$/hydrocarbon separation membrane to separate the PSA tail gas stream and form an $H_2$-rich permeate stream and an $H_2$ depleted non-permeate residue stream.

16 Claims, 2 Drawing Sheets

(52) U.S. Cl.
CPC ............. *C01B 2203/048* (2013.01); *C01B 2203/0415* (2013.01); *C01B 2203/1247* (2013.01); *F25J 2230/08* (2013.01)

(56) References Cited

U.S. PATENT DOCUMENTS

| | | | |
|---|---|---|---|
| 4,333,817 | A | 6/1982 | O'Brien |
| 4,333,820 | A | 6/1982 | Scheifele, Jr. |
| 4,393,259 | A | 7/1983 | Ward |
| 4,673,488 | A | 6/1987 | Turner |
| 5,015,364 | A | 5/1991 | Harandi |
| 5,435,836 | A | 7/1995 | Anand |
| 5,597,404 | A | 1/1997 | Domergue |
| 5,744,681 | A | 4/1998 | Joly |
| 5,856,604 | A | 1/1999 | Stine |
| 6,350,371 | B1 | 2/2002 | Lokhandwala |
| 7,452,458 | B2 | 11/2008 | Sanchez |
| 8,394,174 | B2 | 3/2013 | Chen et al. |
| 8,992,669 | B2 * | 3/2015 | Ikeda .............. B01D 53/22 95/55 |
| 9,327,973 | B1 | 5/2016 | Tsai |
| 9,399,607 | B2 | 7/2016 | Tsai |
| 9,637,427 | B2 | 5/2017 | Tsai |
| 9,663,423 | B2 | 5/2017 | Glover et al. |
| 2014/0086818 | A1 | 3/2014 | Jewell |
| 2015/0086472 | A1 | 3/2015 | Adamopoulos |
| 2015/0218460 | A1 | 8/2015 | Russeff |
| 2016/0115100 | A1 | 4/2016 | Glover |
| 2016/0115101 | A1 | 4/2016 | Yanez |

OTHER PUBLICATIONS

Written Opinion from corresponding PCT application No. PCT/US2020/017880, completed on May 13, 2020.

* cited by examiner

PROCESSES FOR RECOVERING LPG FROM A REFORMING-ZONE EFFLUENT

FIELD OF THE INVENTION

This invention relates generally to reforming hydrocarbons, and more particularly relates to apparatuses and methods for reforming of hydrocarbons with improved recovery of products from a reforming-zone effluent, specifically, LPG and hydrogen.

BACKGROUND OF THE INVENTION

High octane gasoline is needed for modern gasoline engines. Previously, octane numbers were often improved by incorporating various lead-containing additives into the gasoline. As lead-containing additives have been phased out of gasoline for environmental reasons, it has become increasingly necessary to rearrange the structure of the hydrocarbons used in gasoline blending to achieve higher octane ratings. Catalytic reforming of hydrocarbons is a process widely used by refiners for upgrading the octane ratings of gasoline as well as for other useful hydrocarbon conversion applications.

In catalytic reforming, a hydrocarbon feedstock of, for example, $C_5$ hydrocarbons to about $C_{11}$ hydrocarbons, is contacted with a reforming catalyst to convert at least a portion of the heavier hydrocarbons to aromatic hydrocarbons, for example, to increase the octane content of gasoline. The catalytic reforming of the heavier hydrocarbons to produce a reformate that includes aromatic hydrocarbons also produces significant quantities of valuable hydrogen and lighter hydrocarbons, such as liquefied petroleum gas (LPG) containing primarily $C_3$ and $C_4$ hydrocarbons. While originally not necessarily desired, it has become important to maximize the recovery of non-gasoline reforming products, such as, hydrogen and LPG, from the reforming reactor effluent, and to do so effectively and efficiently.

Accordingly, it is desirable to provide apparatuses and methods for reforming of hydrocarbons with improved recovery of products from a reforming reactor effluent. Furthermore, other desirable features and characteristics will become apparent from the subsequent detailed description and the appended claims, taken in conjunction with the accompanying drawings and this background.

SUMMARY OF THE INVENTION

Apparatuses and methods for reforming of hydrocarbons including recovery of products are provided. As indicated above, while reforming reactions provide desirable chemical products, a byproduct of the reactions include $C_3$ and $C_4$ hydrocarbons, as well as hydrogen. More recently, the recovery of these byproducts has become more desirable. The present Applicant has provided processes for recovery of the $C_3$ and $C_4$ hydrocarbons in, for example, U.S. Pat. Nos. 9,327,973, 9,637,427, 9,663,423, and 9,399,607 (the entireties of which are incorporated herein by reference). While effective for their intended purposes, these processes and apparatuses require operation at temperatures that require equipment that is costly to install and utilize. Accordingly, the present processes provide effective and efficient processes for recovering the $C_3$ and $C_4$ hydrocarbons from the reformate effluent without requiring costly equipment.

Therefore, the present invention may be characterized, in at least one aspect, as providing a process for recovering $C_3/C_4$ hydrocarbons from a reformate effluent stream by: separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; cooling the gas stream to a temperature between approximately 15.6 and 71.1° C. (60 and 160° F.) to form a cooled gas stream; cooling the liquid phase hydrocarbon stream to a temperature between approximately 15.6 and 71.1° C. (60 and 160° F.) to form a cooled liquid phase hydrocarbon stream; and, absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream.

The process may include compressing the gas stream prior to cooling the gas stream in a compression zone to a pressure of between approximately 34.5 to 3,447 kPa (5 and 500 psig).

The process may include separating the $C_3/C_4$ enriched liquid phase hydrocarbon stream, in a third separation zone, into a liquid LPG product stream, and an overhead receiver vapor stream and combining the overhead receiver vapor stream with the gas stream. The process may also include splitting the overhead receiver vapor stream into a first portion and a second portion. Only the first portion of the overhead receiver vapor stream may be combined with the gas stream. The process may include adjusting the ratio of the first portion to the second portion. The process may further include cooling the second portion of the overhead receiver vapor stream to a temperature between approximately −28.9 to 26.7° C. (−20 and 80° F.) to provide a cooled second portion and separating the cooled second portion into a second fuel gas stream and a second LPG stream.

All of the liquid phase hydrocarbon stream may be cooled and absorb $C_3/C_4$ hydrocarbons from the cooled tail gas stream.

The second separation zone may include a PSA zone and the gas stream may be a PSA tail gas stream. A temperature of a feed to the PSA zone may be between approximately 15.6 and 71.1° C. (60 and 160° F.) and a pressure of the feed to the PSA zone may be between approximately 1,724 to 7,826 kPa (250 to 700 psig).

The process may also include separating hydrogen, in a membrane separation zone, from the gas stream before cooling the gas stream.

The present invention may be also characterized, in at least one aspect, as providing a process for recovering $C_3/C_4$ hydrocarbons from a reformate effluent stream by: separating, in a first separation zone, a reforming-zone effluent comprising Hz, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; cooling the gas stream to form a cooled gas stream; cooling all of the liquid phase hydrocarbon stream to form a cooled liquid phase hydrocarbon stream; and, absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream.

The process may include separating the $C_3/C_4$ enriched liquid phase hydrocarbon stream, in a third separation zone, into a liquid LPG product stream, and an overhead receiver vapor stream and combining the overhead receiver vapor stream with the gas stream. The process may further include splitting the overhead receiver vapor stream into a first portion and a second portion. Only the first portion of the overhead receiver vapor stream may be combined with the gas stream. The process may also include adjusting the ratio of the first portion to the second portion. The process may include cooling the second portion of the overhead received vapor stream to a temperature between approximately −28.9 to 26.7° C. (−20 and 80° F.) to provide a cooled second portion and separating the cooled second portion into a second fuel gas stream and a second LPG product stream.

The second separation zone may include a PSA zone and the tail gas stream may be a PSA tail gas stream. A temperature of a feed to the PSA zone may be between approximately 15.6 and 71.1° C. (60 and 160° F.) and a pressure of the feed to the PSA zone may be between approximately 1,724 to 7,826 kPa (250 to 700 psig).

The process may include separating hydrogen, in a membrane separation zone, from the gas stream before cooling the gas stream.

The present invention may be further characterized, in at least one aspect, as providing a process for recovering $C_3/C_4$ hydrocarbons from a reformate effluent stream by: separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; separating hydrogen, in a membrane separation zone, from the gas stream to form a second $H_2$ rich-stream and a $H_2$ depleted gas stream; absorbing $C_3/C_4$ hydrocarbons from the $H_2$ depleted gas stream with the liquid phase hydrocarbon stream in an absorbing zone to form a fuel gas stream and a $C_3/C_4$ enriched liquid phase hydrocarbon stream; separating the $C_3/C_4$ enriched liquid phase hydrocarbon stream, in a third separation zone, into a liquid LPG product stream, and an overhead receiver vapor stream; and, combining the overhead receiver vapor stream with the $H_2$ depleted gas stream.

A molar ratio of liquid to gas in the absorbing zone may be greater than 1.

All of the liquid phase hydrocarbon stream may be used to absorb $C_3/C_4$ hydrocarbons from the $H_2$ depleted gas stream.

The absorbing zone may have an operating temperature of between approximately 15.6 and 71.1° C. (60 and 160° F.).

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, the various embodiments contemplated herein relate to apparatuses and methods for the recovery of hydrocarbons products from a reforming effluent. The exemplary embodiments taught herein provide a separation zone in fluid communication with a reforming zone to receive a reforming-zone effluent. As used herein, the term "zone" refers to an area including one or more equipment items and/or one or more sub-zones. Equipment items can include one or more reactors or reactor vessels, scrubbers, strippers, fractionators or distillation columns, absorbers or absorber vessels, adsorber or adsorber vessels, regenerators, heaters, exchangers, coolers/chillers, pipes, pumps, compressors, controllers, membranes, and the like. Additionally, an equipment item can further include one or more zones or sub-zones. The reforming-zone effluent comprises hydrogen ($H_2$), $C_4^-$ hydrocarbons, and $C_5^+$ hydrocarbons including aromatics. As used herein, $C_x$ means hydrocarbon molecules that have "X" number of carbon atoms, $C_x^+$ means hydrocarbon molecules that have "X" and/or more than "X" number of carbon atoms, and $C_x^-$ means hydrocarbon molecules that have "X" and/or less than "X" number of carbon atoms.

The separation zone separates the reforming-zone effluent to form a net gas phase stream and a liquid phase hydrocarbon stream. The net gas phase stream comprises $H_2$ and $C_6^-$ hydrocarbons and the liquid phase hydrocarbon stream comprises $C_5^+$ hydrocarbons. In a separation zone, the net gas phase stream is compressed to provide liquid streams and a gas stream that includes hydrogen. After separating the hydrogen from the gas stream, the liquid stream from the first separation zone is used to absorb any $C_3/C_4$ hydrocarbons remaining in the gas stream. However, unlike prior processes, the temperature in the absorber is higher, requiring less equipment.

With these general principles in mind, one or more embodiments of the present invention will be described with the understanding that the following description is not intended to be limiting.

Figure 1:
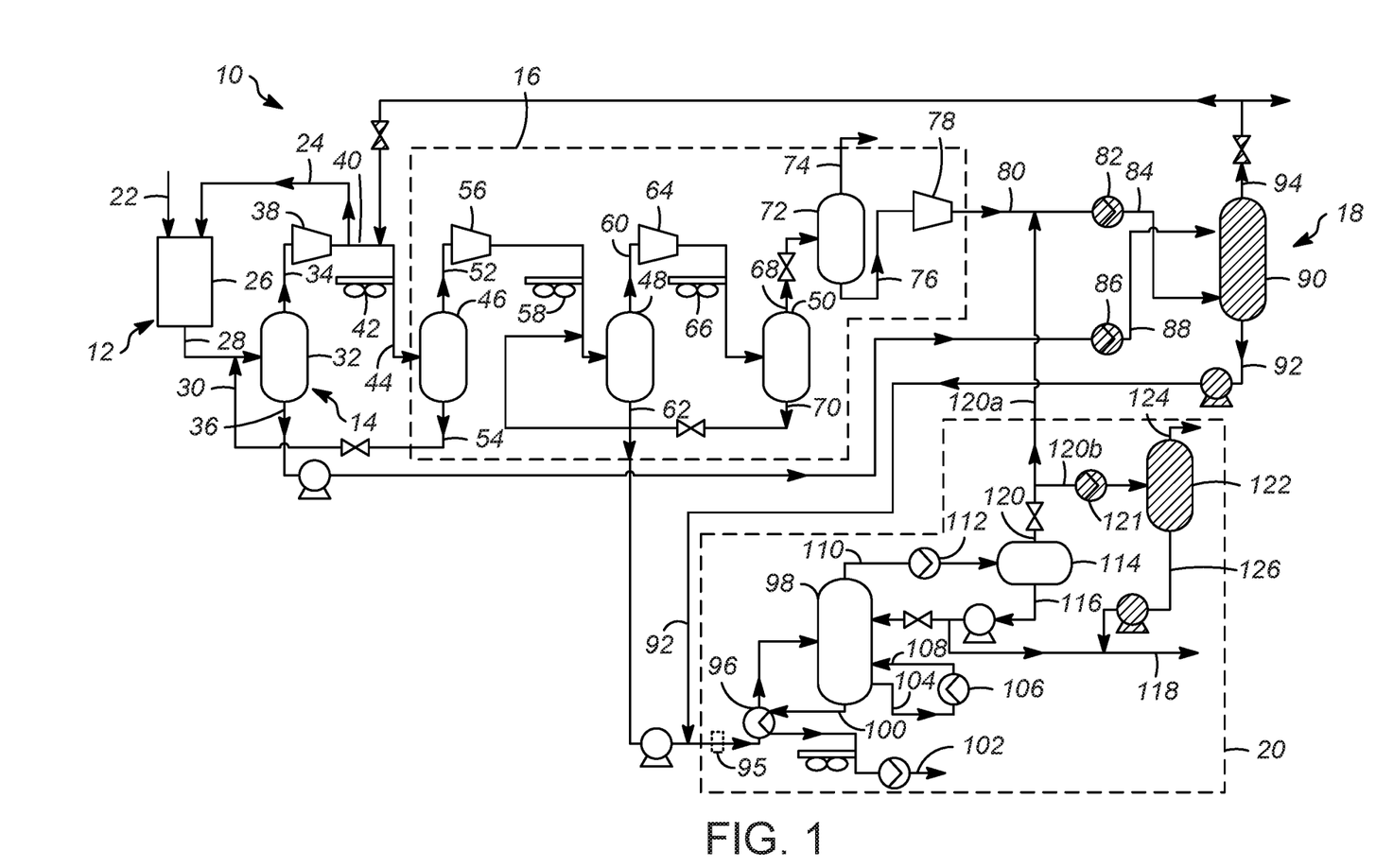
FIG. 1 schematically illustrates an apparatus and a method for reforming of hydrocarbons including recovery of products in accordance with an exemplary embodiment; and, FIG. 2 schematically illustrates an apparatus and a method for reforming of hydrocarbons including recovery of products in accordance with another exemplary embodiment.

Referring to FIG. 1, an apparatus 10 according to various aspects for reforming of hydrocarbons in accordance with an exemplary embodiment is provided. The apparatus 10 includes, generally, a reforming zone 12, a first separation zone 14, a second separation zone 16, an absorption zone 18, and a third separation zone 20.

In exemplary embodiment, a reforming feedstock 22 containing naphtha fraction hydrocarbons, such as from $C_5$ to about $C_{11}$ hydrocarbons with a boiling point range of, for example, from about 70 to about 205° C. (158 and 401° F.), is passed to the reforming zone 12. In the reforming zone 12, the reforming feedstock 22 and a recycle net gas phase stream 24 (discussed in further detail below) are received by a reactor 26 that contains a reforming catalyst as is well-known in the art. The reforming zone 12 may include a plurality of stacked or side-by-side reactors 26 with provisions for intermediate heating of the intermediate reactant stream (e.g., the reforming feedstock 22 and the recycle net gas phase stream 24 including any conversion products formed therefrom) and one or more heat exchangers. In an exemplary embodiment, the recycle net gas phase stream 24 is combined with the reforming feedstock 22 for contact with the reforming catalyst.

A reforming-zone effluent 28 from the reforming zone 12 and contains $H_2$, $C_5^+$ hydrocarbons including aromatics, and lighter hydrocarbons such as $C_4^+$ hydrocarbons including $C_3$ and $C_4$ hydrocarbons. In an exemplary embodiment, the reforming-zone effluent 28 is a two-phase liquid-gas stream in which $H_2$ and the lighter hydrocarbons (e.g., $C_4^-$ hydrocarbons) are predominantly in the gas phase and the heavier hydrocarbons (e.g., $C_5^+$ hydrocarbons including aromatics) are predominantly in the liquid phase. In one embodiment, the reforming-zone effluent 28 has a temperature of from about 35 to about 50° C. and, independently, a pressure of from about 240 to about 830 kPa gauge (34.8 and 120 psig).

The reforming-zone effluent 28, along with a recycle stream 30, is introduced to a separation vessel 32 in the first separation zone 14. In the vessel 32 of the first separation zone 14, the reforming-zone effluent 28 is separated into a net gas phase stream 34 and a liquid phase hydrocarbon stream 36. In an exemplary embodiment, the net gas phase stream 34 comprises $H_2$, $C_6^-$ hydrocarbons, and impurities such as carbon monoxide and/or nitrogen, and the liquid phase hydrocarbon stream 36 comprises $C_5^+$ hydrocarbons including aromatics. In one example, the net gas phase stream 34 comprises $H_2$ present in an amount of from about 80 to about 90 mole %, $C_1$ hydrocarbons present in an amount of about 2 to about 5 mole %, $C_2$ hydrocarbons present in an amount of from about 2 to about 5 mole %, $C_3$ hydrocarbons present in an amount of from about 2 to about 4 mole %, $C_4$ hydrocarbons present in an amount of from about 1.5 to about 2.5 mole %, and possibly some $C_5^+$ hydrocarbons. In another example, the liquid phase hydrocarbon stream 36 comprises $C_5^+$ hydrocarbons present in an amount of from about 90 to about 99.9 mole % and possibly some $C_4^-$ hydrocarbons and $H_2$. In an exemplary embodiment, the separation zone 14 is operated at a temperature of from about 35 to about 50° C. (95 to 122° F.), and, independently, a pressure of from about 240 to about 830 kPa gauge (34.8 to 120 psig).

The net gas phase stream 34 is passed to a compressor 38 to form a compressed net gas phase stream 40. A portion of the compressed net gas phase stream 40 may be used as the recycle net gas phase stream 24. The remaining portion of the compressed net gas phase stream 40 is passed to a cooler 42. In the cooler 42, the compressed net gas phase stream 40 is partially cooled to form a partially cooled, compressed net gas phase stream 44. In an exemplary embodiment, the partially cooled, compressed net gas phase stream 44 has a temperature of from about 30 to about 65° C. (86 to 149° F.) and, independently, a pressure of from about 690 to about 2,460 kPa gauge (100 to 356.8 psig). The partially cooled, compressed net gas phase stream 44 is introduced to the second separation zone 16.

The second separation zone 16 may include multiple vessels 46, 48, 50, which may be a suction drum 46 and recontact drums 48, 50. In the first vessel 46, the partially cooled, compressed net gas phase stream 44 is separated into a first stage vapor stream 52 and a first stage liquid stream 54. The first stage liquid stream 54 may be used as the recycle stream 30 sent to the first separation zone 14. The first stage vapor stream 52 is compressed in a compressor 56, cooled in a cooler 58 and passed to the second vessel 48. In the second vessel 48, the first stage vapor stream 52 is separated into a second stage vapor stream 60 and a second stage liquid stream 62. The second stage vapor stream 60 is compressed in another compressor 64, cooled in another cooler 66 and passed to the third vessel 50. In the third vessel 50, the second stage vapor stream 60 is separated into a third stage vapor stream 68 and a third stage liquid stream 70. The third stage liquid stream 70 may be combined with the second stage liquid stream 62, a portion of which may be recycled to the second vessel 48. The remaining portions of the third stage liquid stream 70 and the second stage liquid stream 62 may be passed to the third separation zone 20 (discussed in more detail below). Any number of separation vessels and stages of compression may be used and this is merely exemplary.

A temperature of the third stage vapor stream 68 is between approximately 15.6 and 71.1° C. (60 and 160° F.) and a pressure of the third stage vapor stream 68 is between approximately 1,724 and 4,826 kPa gauge (250 to 700 psig). The third stage vapor stream 68 may be passed to a PSA zone 72 within the second separation zone 16 for separating the third stage vapor stream 68 into a first $H_2$ rich-stream 74 and a tail gas stream 76. In an exemplary embodiment, the PSA zone 72 contains an adsorbent (e.g., adsorbent material(s)) and is configured for contacting the third stage vapor stream 68 with the adsorbent for selectively separating $H_2$ from hydrocarbons (e.g., $C_4^-$ hydrocarbons) and impurities such as carbon monoxide and/or nitrogen to form the first $H_2$ rich-stream 74. The exemplary PSA zone 72 operates on the principle of selectively adsorbing hydrocarbons and/or other impurities (e.g., carbon monoxide and/or nitrogen) onto the adsorbent at a relatively high pressure (e.g., about 1,920 to about 5,520 kPa gauge (280 to 800 psig) to form the first $H_2$ rich-stream 74, and desorbing the hydrocarbons from the adsorbent at relatively low pressure (e.g., about 10 to about 500 kPa gauge (1.45 to 72.5 psig)) to regenerate the adsorbent and to form a tail gas stream 76 that contains the hydrocarbons and/or other impurities (e.g., carbon monoxide and/or nitrogen).

In an exemplary embodiment, the PSA zone 72 includes a plurality of fixed-bed adsorption units each containing layers of different adsorbent materials where the lower layer or layers are filled with weaker adsorbent materials, e.g., relatively low affinity for adsorbing gaseous hydrocarbons, and the upper layer or layers are filled with stronger adsorbent materials, e.g., relatively high affinity for adsorbing gaseous hydrocarbons (e.g., gaseous $C_3^-$ hydrocarbons) and impurities (e.g., carbon monoxide and/or nitrogen). For example, the lower layer(s) can contain weakly adsorbent materials, such as activated alumina and/or silica gel, while the intermediate layer(s) can contain intermediate strength adsorbent materials, such as activated carbon, and the upper layer(s) can contain strong adsorbent materials, such as zeolite and/or molecular sieve materials. In an exemplary embodiment, the multiple fixed-bed adsorption units cooperatively operate in a staggered sequence to produce constant feed (e.g., stream 68), product (e.g., stream 74), and tail gas (e.g., stream 76) flows. In an exemplary embodiment, the PSA zone 72 operates following a five-step pressure-swing cycle including an adsorption step, a co-current depressurization step, a counter-current depressurization step, a purge step, and a repressurization step. During the adsorption step, the third stage vapor stream 68 enters a lower portion of the fixed-bed adsorption unit at a relatively high pressure, and as the feed gas rises in the unit, the hydrocarbons and impurities (e.g., carbon monoxide and/or nitrogen) are adsorbed in the various layers of the adsorbent materials depending upon their respective adsorption selectivity to form the first $H_2$ rich-stream 74. The co-current depressurization, counter-current depressurization and purge steps decrease the pressure in the fixed-bed adsorption unit and purge the unit with high purity gas from the product (e.g., first $H_2$ rich-stream 74) or co-current depressurization steps, respectively, to remove the hydrocarbons and impurities (e.g., carbon monoxide and/or nitrogen) and regenerate the adsorption materials. The repressurization step increases the pressure in the fixed-bed adsorption unit with either feed gas (e.g., tail gas stream 76) or product gas (e.g., the first $H_2$ rich-stream 74) in preparation for the next adsorption step. Other pressure swing adsorption configurations for recovering hydrogen in the PSA zone 72 known to those skilled in the art may also be used.

In an exemplary embodiment, first $H_2$ rich-stream 74 comprises $H_2$ present in an amount of from about 90 to less than 100 mole %, such as from about 90 to about 99.999 mole %, such as from about 95 to about 99.999 mole %, such as from about 98 to about 99.999 mole %, such as from about 99 to about 99.999 mole %, for example about 99.99 mole %, and possibly some $C_2$— hydrocarbons and impurities (e.g., carbon monoxide and/or nitrogen). In an exemplary embodiment, the tail gas stream 76 comprises $C_2$— hydrocarbons present in an amount of from about 25 to about 80 mole %, $H_2$ present in an amount of from about 25 to about 75 mole %, and some $C_3^+$ hydrocarbons and impurities (e.g., carbon monoxide and/or nitrogen).

The first $H_2$ rich-stream 74 is removed from the apparatus 10, for example, to be used as a hydrogen product stream. The tail gas stream 76 is passed through a compressor 78 to form a compressed tail gas stream 80 that is further advanced through a cooler 82 to partially cool the compressed tail gas stream 80 and form a partially cooled, compressed PSA tail gas stream 84. The compressed tail gas stream 80 may be cooled to a temperature between 15.6 and 71.1° C. (60 and 160° F.). The partially cooled, compressed PSA tail gas stream 84 is passed to the absorption zone 18.

As shown in FIG. 1, the absorption zone 18 also receives the liquid phase hydrocarbon stream 36 from the first separation zone 14. Specifically, the liquid phase hydrocarbon stream 36 is cooled in a cooler 86 to form a cooled, liquid phase hydrocarbon stream 88. The cooled, liquid phase hydrocarbon stream 88 is introduced into the absorption zone 18.

In an exemplary embodiment, the partially cooled, compressed PSA tail gas stream 84 is introduced to a lower portion of an absorber vessel 90 in the absorption zone 18 and rises upwardly while the cooled, liquid phase hydrocarbon stream 88 is introduced to an upper portion of the absorber vessel 90 and descends downwardly for countercurrent contact with the partially cooled, compressed PSA tail gas stream 84. During contact in the absorber vessel 90, $C_3/C_4$ hydrocarbons from the partially cooled, compressed PSA tail gas stream 84 are extracted and/or absorbed to the cooled, liquid phase hydrocarbon stream 88 to form an $C_3/C_4$ enriched liquid phase hydrocarbon stream 92. In addition to $C_3/C_4$ hydrocarbons, the $C_3/C_4$ enriched liquid phase hydrocarbon stream 92 may include $C_5^+$ hydrocarbons. A fuel gas stream 94 including some $H_2$, $C_2^-$ hydrocarbons is also recovered from the absorber vessel 90, a portion of which may be combined with the compressed net gas phase stream 40.

As indicated above, unlike prior processes, the operating temperature of the absorber vessel 90 is higher than prior processes. An exemplary temperature range for the absorber vessel 90 is between approximately 15.6 and 71.1° C. (60 and 160° F.). This means that the present processes and apparatuses do not require equipment such as, chillers and vapor driers required in prior processes. However, merely changing the temperature will not ensure that the $C_3/C_4$ hydrocarbons are recovered from the partially cooled, compressed PSA tail gas stream 84. Accordingly, in the present processes, the pressure of the compressed PSA tail gas stream 80 is between approximately 34.5 and 3,447 kPa gauge (5 and 500 psig), or preferably between 689 and 2,068 kPa (100 and 300 psig). Further, in the present processes the entirety of the liquid phase hydrocarbon stream 36 to ensure the $C_3/C_4$ hydrocarbons are recovered. In the present processes, it is preferred that the molar ratio of liquid to vapor in the absorber vessel 90 is at least 1, and may be greater than 1, for example, 1.33, 1.41 or even higher.

In order to recover the reformate products and LPG in the $C_3/C_4$ enriched liquid phase hydrocarbon stream 92, the $C_3/C_4$ enriched liquid phase hydrocarbon stream 92, along with portions of the third stage liquid stream 70 and the second stage liquid stream 62 from the second separation zone 16 (hereinafter simply the $C_3/C_4$ enriched liquid phase hydrocarbon stream 92), are passed to the third separation zone 20. A drier 95 may optionally be used to remove any water (discussed below).

After being heated in a heat exchanger 96, the $C_3/C_4$ enriched liquid phase hydrocarbon stream 92, is passed to a separation column 98, for example a debutanizer column. A bottoms stream 100 from the separation column 98 may be sent to the heat exchanger 96, cooled, and exchanged with other streams to receive heat and provide a reformate product stream 102. A reboiling portion 104 may be heated with steam or hot oil in a heat exchanger 106 to provide a reboiled portion 108, which may supply heat to the separation column 98 for separating the components therein. An overhead stream 110 may be cooled in a heat exchanger 112 and passed to a receiver 114. A receiver bottoms 116 may be recovered from the receiver 114, with a portion being refluxed back to the separation column 98 and a second portion forming an LPG product stream 118. The operating temperature of the heat exchanger 112, which can range between −28.9 to 26.7° C. (−20 and 80° F.), will determine whether or not to include the drier 95, mentioned above. Specifically, if the temperature is below 15.5° C. (60° F.), the drier 95 may not be required since at that temperature the likelihood to form hydrates is low.

All, a portion 120*a*, or none of a receiver overhead stream 120 may be passed to the absorption zone 18, for example by being combined with the compressed tail gas stream 80. It is also contemplated that all, a portion 120*b*, or none of the receiver overhead stream 120 is passed to a separation vessel 122, for example a flash drum (or other separation vessel), to separate into a vapor stream 124 including any remaining $H_2$ and $C_2^-$ hydrocarbons and a liquid stream 126 which includes $C_3/C_4$ hydrocarbons, which can be recovered in the LPG product stream 118.

Accordingly, it is contemplated, but not required, that at least some of the receiver overhead stream 120 is recycled to the absorption zone 18. Additionally, it is contemplated that all of the receiver overhead stream 120 is recycled to the absorption zone 18, and the separation vessel 122 may be eliminated. Alternatively, as indicted above, none of the receiver overhead stream 120 may be recycled to the absorption zone 18. It is contemplated that a ratio of the portion 120*a* of the receiver overhead stream 120 passed to the absorption zone 18 compared to the portion 120*b* of the receiver overhead stream 120 passed to the separation vessel 122 is adjusted based on one or more operating parameters or conditions.

Figure 2:
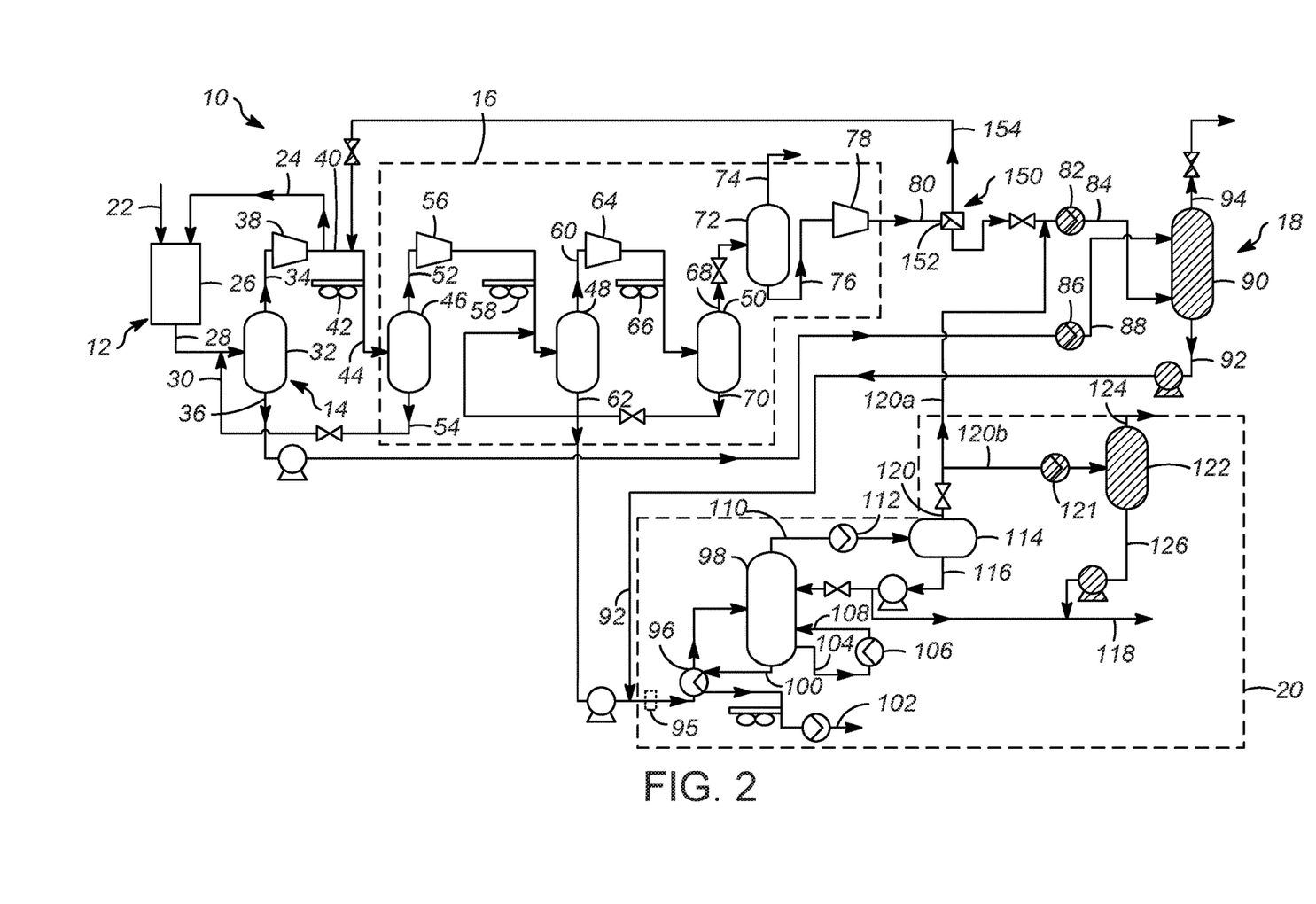

As mentioned above, the present processes provide a first $H_2$ rich-stream 74 which may be recovered as a hydrogen product stream to be used in various processes that are hydrogen dependent. However, additional or increased recovery of hydrogen and potentially additional or increased recovery of LPG is provided in the embodiment of FIG. 2. In this depicted embodiment, the apparatus 10 further comprises a membrane separation zone 150. In FIG. 2, identical reference numerals are used with identical elements, and the above description is hereby incorporated by referenced.

As mentioned above, the tail gas stream 76 still includes some level of hydrogen. Accordingly, after being compressed in compressor 78, but before being cooled in the cooler 82, the tail gas stream may be passed to the membrane separation zone 150. The membrane separation zone 150 includes an $H_2$/hydrocarbon separation membrane 152 that is selectively permeable to $H_2$ while being effectively non-permeable to hydrocarbons, e.g., $C_4^-$ hydrocarbons and impurities (e.g., carbon monoxide and/or nitrogen). In commercially available embodiments, the $H_2$/hydrocarbon separation membrane 152 may be in the form of either spiral wound or hollow fibers, made of cellulose acetate, cellulose triacetate, polyimide, polysulfone material or any other suitable material. Such fibers may be assembled into compact bundles to provide a large membrane area available for the passage of the desired product gas (Hz) therethrough. Alternatively, the $H_2$/hydrocarbon separation membrane 152 can be any other separation membrane known to those skilled in the art for separating $H_2$, hydrocarbons, and impurities (e.g., carbon monoxide and/or nitrogen). In an exemplary embodiment, the $H_2$/hydrocarbon separation membrane 152 has a selectivity of at least about 60, preferably at least about 75, for example from about 75 to about 370 or greater, of $H_2$ over $C_4^-$ hydrocarbons, and other impurities such as CO, $N_2$ and the like. Accordingly, a second $H_2$ rich-stream 154 is provided by the membrane separation zone 150 as a permeate, while a retentate from the membrane separation zone 150 is passed to the cooler 82 to partially cool the compressed tail gas stream 80 and form a partially cooled, compressed PSA tail gas stream 84. As shown in FIG. 2, the second $H_2$ rich-stream 154 may be combined with the compressed net gas phase stream 40 from the first separation zone 14. As mentioned above, the use of the membrane separation zone 150 provides for increased recovery of hydrogen instead of being lost in a fuel gas stream.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Specific Embodiments

While the following is described in conjunction with specific embodiments, it will be understood that this description is intended to illustrate and not limit the scope of the preceding description and the appended claims.

A first embodiment of the invention is a process for recovering $C_3/C_4$ hydrocarbons from a reformate effluent stream, the process comprising separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; cooling the gas stream to a temperature between approximately 15.6 and 71.1° C. (60 and 160° F.) to form a cooled gas stream; cooling the liquid phase hydrocarbon stream to a temperature between approximately 15.6 and 71.1° C. (60 and 160° F.) to form a cooled liquid phase hydrocarbon stream; and, absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream. An embodiment of the invention is one, any or all of prior embodiments in this paragraph up through the first embodiment in this paragraph further comprising compressing the gas stream prior to cooling the gas stream in a compression zone to a pressure of between approximately 34.5 to 3,447 kPa (5 and 500 psig). An embodiment of the invention is one, any or all of prior embodiments in this paragraph up through the first embodiment in this paragraph further comprising separating the $C_3/C_4$ enriched liquid phase hydrocarbon stream, in a third separation zone, into a liquid LPG product stream, and an overhead receiver vapor stream; and, combining the overhead receiver vapor stream with the gas stream. An embodiment of the invention is one, any or all of prior embodiments in this paragraph up through the first embodiment in this paragraph further comprising splitting the overhead receiver vapor stream into a first portion and a second portion, wherein only the first portion of the overhead receiver vapor stream is combined with the gas stream. An embodiment of the invention is one, any or all of prior embodiments in this paragraph up through the first embodiment in this paragraph further comprising adjusting the ratio of the first portion to the second portion. An embodiment of the invention is one, any or all of prior embodiments in this paragraph up through the first embodiment in this paragraph further comprising cooling the second portion of the overhead receiver vapor stream to a temperature between approximately −28.9 to 26.7° C. (−20 and 80° F.) to provide a cooled second portion; and, separating the cooled second portion into a second fuel gas stream and a second LPG stream. An embodiment of the invention is one, any or all of prior embodiments in this paragraph up through the first embodiment in this paragraph, wherein all of the liquid phase hydrocarbon stream is cooled and absorbs $C_3/C_4$ hydrocarbons from the cooled tail gas stream. An embodiment of the invention is one, any or all of prior embodiments in this paragraph up through the first embodiment in this paragraph wherein the second separation zone comprises a PSA zone and the gas stream comprises a PSA tail gas stream, and wherein a temperature of a feed to the PSA zone is between approximately 15.6 and 71.1° C. (60 and 160° F.) and a pressure of the feed to the PSA zone is between approximately 1,724 to 7,826 kPa (250 to 700 psig). An embodiment of the invention is one, any or all of prior embodiments in this paragraph up through the first embodiment in this paragraph further comprising separating hydrogen, in a membrane separation zone, from the gas stream before cooling the gas stream.

A second embodiment of the invention is a process for recovering $C_3/C_4$ hydrocarbons from a reformate effluent stream, the process comprising separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; cooling the gas stream to form a cooled gas stream; cooling all of the liquid phase hydrocarbon stream to form a cooled liquid phase hydrocarbon stream; and, absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream. An embodiment of the invention is one, any or all of prior embodiments in this paragraph up through the second embodiment in this paragraph further comprising separating the $C_3/C_4$ enriched liquid phase hydrocarbon stream, in a third separation zone, into a liquid LPG product stream, and an overhead receiver vapor stream; and, combining the overhead receiver vapor stream with the gas stream. An embodiment of the invention is one, any or all of prior embodiments in this paragraph up through the second embodiment in this paragraph further comprising splitting the overhead receiver vapor stream into a first portion and a second portion, wherein only the first portion of the overhead receiver vapor stream is combined with the gas stream. An embodiment of the invention is one, any or all of prior embodiments in this paragraph up through the second embodiment in this paragraph further comprising adjusting the ratio of the first portion to the second portion. An embodiment of the invention is one, any or all of prior embodiments in this paragraph up through the second embodiment in this paragraph further comprising cooling the second portion of the overhead received vapor stream to a temperature between approximately −28.9 to 26.7° C. (−20 and 80° F.) to provide a cooled second portion; and, separating the cooled second portion into a second fuel gas stream and a second LPG product stream. An embodiment of the invention is one, any or all of prior embodiments in this paragraph up through the second embodiment in this paragraph wherein the second separation zone comprises a PSA zone and the tail gas stream comprises a PSA tail gas stream, and wherein a temperature of a feed to the PSA zone is between approximately 15.6 and 71.1° C. (60 and 160° F.) and a pressure of the feed to the PSA zone is between approximately 1,724 to 7,826 kPa (250 to 700 psig). An embodiment of the invention is one, any or all of prior embodiments in this paragraph up through the second embodiment in this paragraph further comprising separating hydrogen, in a membrane separation zone, from the gas stream before cooling the gas stream.

A third embodiment of the invention is a process for recovering $C_3/C_4$ hydrocarbons from a reformate effluent stream, the process comprising separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics; separating, in a second separation zone, the net gas phase stream to form a first $H_2$ rich-stream and a gas stream that comprises $H_2$, and $C_4^-$ hydrocarbons; separating hydrogen, in a membrane separation zone, from the gas stream to form a second $H_2$ rich-stream and a $H_2$ depleted gas stream; absorbing $C_3/C_4$ hydrocarbons from the $H_2$ depleted gas stream with the liquid phase hydrocarbon stream in an absorbing zone to form a fuel gas stream and a $C_3/C_4$ enriched liquid phase hydrocarbon stream; separating the $C_3/C_4$ enriched liquid phase hydrocarbon stream, in a third separation zone, into a liquid LPG product stream, and an overhead receiver vapor stream; and, combining the overhead receiver vapor stream with the $H_2$ depleted gas stream. An embodiment of the invention is one, any or all of prior embodiments in this paragraph up through the third embodiment in this paragraph, wherein a molar ratio of liquid to gas in the absorbing zone is greater than 1 An embodiment of the invention is one, any or all of prior embodiments in this paragraph up through the third embodiment in this paragraph, wherein all of the liquid phase hydrocarbon stream absorbs $C_3/C_4$ hydrocarbons from the $H_2$ depleted gas stream. An embodiment of the invention is one, any or all of prior embodiments in this paragraph up through the third embodiment in this paragraph, wherein the absorbing zone has an operating temperature of between approximately 15.6 and 71.1° C. (60 and 160° F.).

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for recovering $C_3/C_4$ hydrocarbons from a reformate effluent stream, the process comprising:
   separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics;
   separating, in a second separation zone, the net gas phase stream to form a first $H_2$ rich-stream and a gas stream that comprises $H_2$, and $C_4^-$ hydrocarbons;
   cooling the gas stream to a temperature between approximately 15.6 and 71.1° C. (60 and 160° F.) to form a cooled gas stream;
   cooling the liquid phase hydrocarbon stream to a temperature between approximately 15.6 and 71.1° C. (60 and 160° F.) to form a cooled liquid phase hydrocarbon stream;
   absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream;
   separating the $C_3/C_4$ enriched liquid phase hydrocarbon stream, in a third separation zone, into a liquid LPG product stream, and an overhead receiver vapor stream;
   splitting the overhead receiver vapor stream into a first portion and a second portion; and
   combining only the first portion of the overhead receiver vapor stream with the gas stream.

2. The process of claim 1 further comprising:
   compressing the gas stream prior to cooling the gas stream in a compression zone to a pressure of between approximately 34.5 to 3,447 kPa (5 and 500 psig).

3. The process of claim 1 further comprising:
   adjusting a ratio of the first portion to the second portion.

4. The process of claim 1 further comprising:
   cooling the second portion of the overhead receiver vapor stream to a temperature between approximately −28.9 to 26.7° C. (−20 and 80° F.) to provide a cooled second portion; and,
   separating the cooled second portion into a second fuel gas stream and a second LPG stream.

5. The process of claim 1, wherein all of the liquid phase hydrocarbon stream is cooled and absorbs $C_3/C_4$ hydrocarbons from the cooled gas stream.

6. The process of claim 1 wherein the second separation zone comprises a PSA zone and the gas stream comprises a PSA tail gas stream, and wherein a temperature of a feed to the PSA zone is between approximately 15.6 and 71.1° C. (60 and 160° F.) and a pressure of the feed to the PSA zone is between approximately 1,724 to 7,826 kPa (250 to 700 psig).

7. The process of claim 1 further comprising:
   separating hydrogen, in a membrane separation zone, from the gas stream before cooling the gas stream.

8. A process for recovering $C_3/C_4$ hydrocarbons from a reformate effluent stream, the process comprising:
   separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics;
   separating, in a second separation zone, the net gas phase stream to form a first $H_2$ rich-stream and a gas stream that comprises $H_2$, and $C_4^+$ hydrocarbons;
   cooling the gas stream to form a cooled gas stream;
   cooling all of the liquid phase hydrocarbon stream to form a cooled liquid phase hydrocarbon stream;
   absorbing $C_3/C_4$ hydrocarbons from the cooled gas stream with the cooled liquid phase hydrocarbon stream in an absorbing zone to form a fuel gas stream and a $C_3/C_4$ enriched liquid phase hydrocarbon stream;
   separating the $C_3/C_4$ enriched liquid phase hydrocarbon stream, in a third separation zone, into a liquid LPG product stream, and an overhead receiver vapor stream;
   splitting the overhead receiver vapor stream into a first portion and a second portion; and
   combining only the first portion of the overhead receiver vapor stream with the gas stream.

9. The process of claim 8 further comprising:
   adjusting a ratio of the first portion to the second portion.

10. The process of claim 8 further comprising:
    cooling the second portion of the overhead received vapor stream to a temperature between approximately −28.9 to 26.7° C. (−20 and 80° F.) to provide a cooled second portion; and,
    separating the cooled second portion into a second fuel gas stream and a second LPG product stream.

11. The process of claim 8 wherein the second separation zone comprises a PSA zone and the gas stream comprises a PSA tail gas stream, and wherein a temperature of a feed to the PSA zone is between approximately 15.6 and 71.1° C. (60 and 160° F.) and a pressure of the feed to the PSA zone is between approximately 1,724 to 7,826 kPa (250 to 700 psig).

12. The process of claim 8 further comprising:
    separating hydrogen, in a membrane separation zone, from the gas stream before cooling the gas stream.

13. A process for recovering $C_3/C_4$ hydrocarbons from a reformate effluent stream, the process comprising:
    separating, in a first separation zone, a reforming-zone effluent comprising $H_2$, $C_4^-$ hydrocarbons, and $C_5^+$ hydrocarbons, including aromatics, to form a net gas phase stream comprising $C_6^-$ hydrocarbons and $H_2$ and a liquid phase hydrocarbon stream comprising $C_5^+$ hydrocarbons including aromatics;
    separating, in a second separation zone, the net gas phase stream to form a first $H_2$ rich-stream and a gas stream that comprises $H_2$, and $C_4^-$ hydrocarbons;
    separating hydrogen, in a membrane separation zone, from the gas stream to form a second $H_2$ rich-stream and a $H_2$ depleted gas stream;
    absorbing $C_3/C_4$ hydrocarbons from the $H_2$ depleted gas stream with the liquid phase hydrocarbon stream in an absorbing zone to form a fuel gas stream and a $C_3/C_4$ enriched liquid phase hydrocarbon stream;
    separating the $C_3/C_4$ enriched liquid phase hydrocarbon stream, in a third separation zone, into a liquid LPG product stream, and an overhead receiver vapor stream;
    splitting the overhead receiver vapor stream into a first portion and a second portion; and
    combining only the first portion of the overhead receiver vapor stream with the $H_2$ depleted gas stream.

14. The process of claim 13, wherein a molar ratio of liquid to gas in the absorbing zone is greater than 1.

15. The process of claim 13, wherein all of the liquid phase hydrocarbon stream absorbs $C_3/C_4$ hydrocarbons from the $H_2$ depleted gas stream.

16. The process of claim 13, wherein the absorbing zone has an operating temperature of between approximately 15.6 and 71.1° C. (60 and 160° F.).

* * * * *